US012124625B1

(12) United States Patent
Wu et al.

(10) Patent No.: US 12,124,625 B1
(45) Date of Patent: Oct. 22, 2024

(54) PUPIL DYNAMICS, PHYSIOLOGY, AND CONTEXT FOR ESTIMATING VIGILANCE

(71) Applicant: Rockwell Collins, Inc., Cedar Rapids, IA (US)

(72) Inventors: Peggy Wu, Ellicott City, MD (US); Brigid A. Blakeslee, Hamden, CT (US); Andrew Radlbeck, South Glastonbury, CT (US); Ganesh Sundaramoorthi, Duluth, GA (US)

(73) Assignee: Rockwell Collins, Inc., Cedar Rapids, IA (US)

( * ) Notice: Subject to any disclaimer, the term of this patent is extended or adjusted under 35 U.S.C. 154(b) by 0 days.

(21) Appl. No.: 18/216,841

(22) Filed: Jun. 30, 2023

(51) Int. Cl.
*G06F 3/01* (2006.01)

(52) U.S. Cl.
CPC .................................. *G06F 3/013* (2013.01)

(58) Field of Classification Search
CPC ....................................................... G06F 3/013
See application file for complete search history.

(56) References Cited

U.S. PATENT DOCUMENTS

| | | | | |
|---|---|---|---|---|
| 7,809,160 | B2 * | 10/2010 | Vertegaal | G06F 3/013 |
| | | | | 345/157 |
| 9,471,763 | B2 * | 10/2016 | Norden | G06V 40/18 |
| 9,704,038 | B2 * | 7/2017 | Wu | G06F 3/013 |
| 10,043,281 | B2 * | 8/2018 | Mallinson | G06T 7/20 |
| 10,192,110 | B2 * | 1/2019 | Chen | G06V 10/143 |
| 10,521,012 | B2 * | 12/2019 | Liu | G06V 40/10 |
| 10,528,127 | B2 * | 1/2020 | Caraffi | G06F 3/013 |
| 11,055,530 | B2 * | 7/2021 | Kaehler | G06F 3/013 |
| 11,132,055 | B2 * | 9/2021 | Jones | G02B 27/0093 |
| 11,506,888 | B2 * | 11/2022 | Whitmire | G02B 27/0101 |
| 11,645,932 | B2 * | 5/2023 | Bertolli | A61B 5/7267 |
| | | | | 434/131 |
| 11,881,294 | B2 * | 1/2024 | Gross | G06F 3/013 |
| 2005/0175218 | A1 * | 8/2005 | Vertegaal | G06T 7/254 |
| | | | | 345/157 |
| 2013/0188032 | A1 * | 7/2013 | Vertegaal | H04N 7/18 |
| | | | | 348/78 |
| 2013/0293467 | A1 * | 11/2013 | Norden | G06F 21/32 |
| | | | | 345/173 |

(Continued)

FOREIGN PATENT DOCUMENTS

NL            2022016 B1      5/2021

*Primary Examiner* — Michael J Jansen, II
(74) *Attorney, Agent, or Firm* — Suiter Swantz IP

(57) ABSTRACT

A computer system records eye tracking data and identifies movements in the eye tracking data to determine gaze and pupil dynamics. Eye tracking data is correlated with a current task and predetermined vigilance requirements. The system determines if the user is exhibiting an appropriate level of vigilance based on the task or is becoming fixated. When fixation is detected, the system may engage in remedial action. A task flow diagram represents the operator tasks. Interactions between the user and the instrumentation are used to estimate the probability distribution of the task the user is currently conducting. The system correlates eye tracking data and physiological data such as electroencephalogram (EEG) and functional near-infrared spectroscopy (fNIRs) to determine neuroactivity. Monitoring neuroactivity reduces the probability of a false positive for fixation.

15 Claims, 5 Drawing Sheets

(56) References Cited

U.S. PATENT DOCUMENTS

| | | | |
|---|---|---|---|
| 2016/0196465 A1* | 7/2016 | Wu | G06F 3/013 |
| | | | 382/203 |
| 2016/0274659 A1* | 9/2016 | Caraffi | H04N 23/90 |
| 2016/0364881 A1* | 12/2016 | Mallinson | G06T 7/20 |
| 2017/0351899 A1* | 12/2017 | Chen | G06V 40/19 |
| 2018/0052514 A1* | 2/2018 | Liu | G06V 40/10 |
| 2018/0276467 A1* | 9/2018 | Kaehler | G02B 27/0172 |
| 2019/0179409 A1* | 6/2019 | Jones | G02B 27/0172 |
| 2021/0088784 A1 | 3/2021 | Whitmire et al. | |
| 2022/0301669 A1 | 9/2022 | Gross et al. | |
| 2022/0327945 A1 | 10/2022 | Bertolli et al. | |
| 2023/0116198 A1 | 4/2023 | Krüger et al. | |
| 2023/0400917 A1* | 12/2023 | Lundahl | G06F 3/013 |

* cited by examiner

PUPIL DYNAMICS, PHYSIOLOGY, AND CONTEXT FOR ESTIMATING VIGILANCE

BACKGROUND

Situation awareness is difficult to measure. Measuring one's situation awareness often requires pausing training or simulation exercises, and administering self-report surveys. This process is time consuming, and can take a trainee out of a simulation, affecting the realism of the experience. However, assessing the operator's level of situation awareness in situ is important for assessing their competency and readiness.

Gaze and eye movements are key indicators of pilot attention. While pilots must continuously scan different areas to maintain situation awareness, sustained attention is needed for tasks such as target recognition and tracking. When a pilot monitoring system is evaluating whether a pilot is exhibiting fixation or attention tunneling, the system can mistake a pilot who is exhibiting sustained attention for target tracking as fixation or attention tunneling.

Consequently, it would be advantageous if an apparatus existed that is suitable for monitoring a trainee's situational awareness during a training operation and distinguishing between appropriate sustained attention and fixation.

SUMMARY

In one aspect, embodiments of the inventive concepts disclosed herein are directed to a computer system that records eye tracking data. The system identifies movements in the eye tracking data to determine gaze and pupil dynamics. Eye tracking data is correlated with a current task and predetermined vigilance requirements. The system determines if the user is exhibiting an appropriate level of vigilance based on the task or is becoming fixated. When fixation is detected, the system may engage in remedial action.

In a further aspect, a task flow diagram represents the operator tasks. Interactions between the user and the instrumentation are used to estimate the probability distribution of the task the user is currently conducting.

In a further aspect, the system correlates eye tracking data and physiological data such as electroencephalogram (EEG) and functional near-infrared spectroscopy (fNIRs) to determine neuroactivity. Monitoring neuroactivity reduces the probability of a false positive for fixation.

It is to be understood that both the foregoing general description and the following detailed description are exemplary and explanatory only and should not restrict the scope of the claims. The accompanying drawings, which are incorporated in and constitute a part of the specification, illustrate exemplary embodiments of the inventive concepts disclosed herein and together with the general description, serve to explain the principles.

BRIEF DESCRIPTION OF THE DRAWINGS

The numerous advantages of the embodiments of the inventive concepts disclosed herein may be better understood by those skilled in the art by reference to the accompanying figures in which.

DETAILED DESCRIPTION

Figure 1:
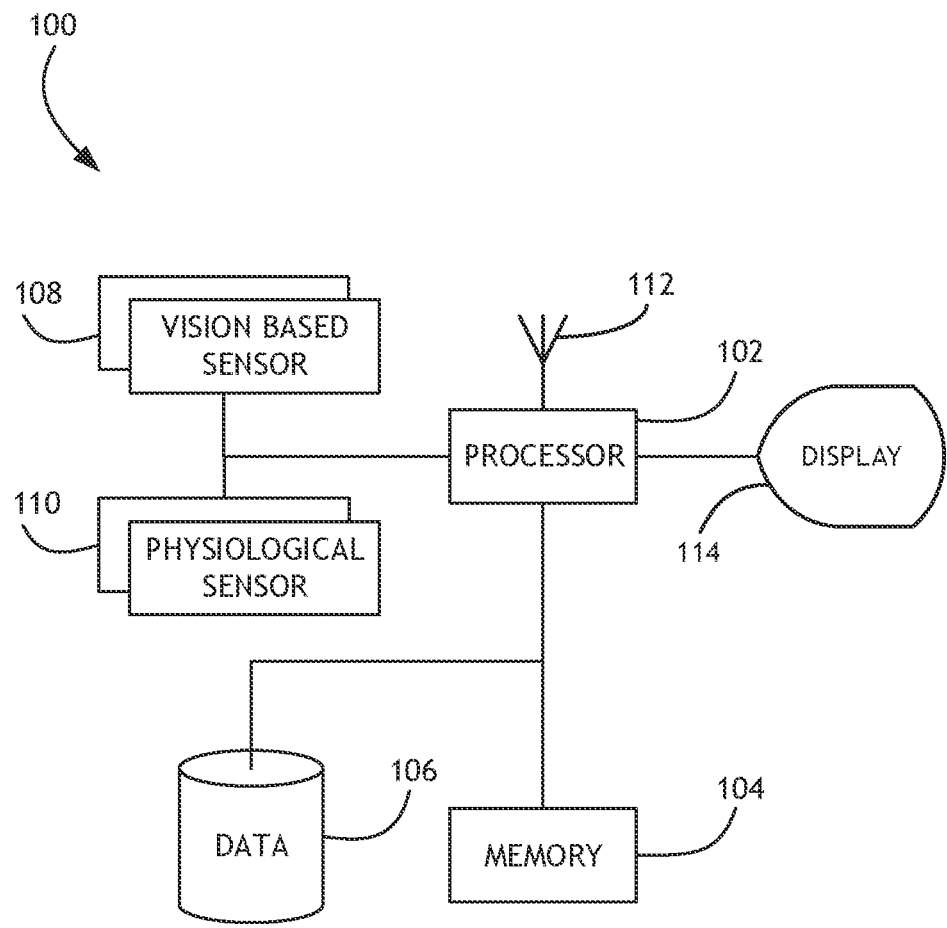
FIG. 1 shows a block diagram of a system suitable for implementing embodiments of the incentive concepts disclosed herein.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. In the following detailed description of embodiments of the instant inventive concepts, numerous specific details are set forth in order to provide a more thorough understanding of the inventive concepts. However, it will be apparent to one of ordinary skill in the art having the benefit of the instant disclosure that the inventive concepts disclosed herein may be practiced without these specific details. In other instances, well-known features may not be described in detail to avoid unnecessarily complicating the instant disclosure. The inventive concepts disclosed herein are capable of other embodiments or of being practiced or carried out in various ways. Also, it is to be understood that the phraseology and terminology employed herein is for the purpose of description and should not be regarded as limiting.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only, and should not be construed to limit the inventive concepts disclosed herein in any way unless expressly stated to the contrary.

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of embodiments of the instant inventive concepts. This is done merely for convenience and to give a general sense of the inventive concepts, and "a' and "an" are intended to include one or at least one and the singular also includes the plural unless it is obvious that it is meant otherwise.

Finally, as used herein any reference to "one embodiment," or "some embodiments" means that a particular element, feature, structure, or characteristic described in connection with the embodiment is included in at least one embodiment of the inventive concepts disclosed herein. The appearances of the phrase "in some embodiments" in various places in the specification are not necessarily all referring to the same embodiment, and embodiments of the inventive concepts disclosed may include one or more of the features expressly described or inherently present herein, or any combination of sub-combination of two or more such features, along with any other features which may not necessarily be expressly described or inherently present in the instant disclosure.

Broadly, embodiments of the inventive concepts disclosed herein are directed to a computer system that records eye tracking data. The system identifies movements in the eye tracking data to determine gaze and pupil dynamics. Eye tracking data is correlated with a current task and predetermined vigilance requirements. The system determines if the user is exhibiting an appropriate level of vigilance based on the task or is becoming fixated. When fixation is detected, the system may engage in remedial action. A task flow diagram represents the operator tasks. Interactions between the user and the instrumentation are used to estimate the probability distribution of the task the user is currently conducting. The system correlates eye tracking data and physiological data such as electroencephalogram (EEG) and functional near-infrared spectroscopy (fNIRs) to determine neuroactivity. Monitoring neuroactivity reduces the probability of a false positive for fixation.

This invention uses data of a pilot's eyes to detect their gaze and pupil dynamics, coupled with knowledge about their current task to differentiate between a pilot exhibiting task appropriate vigilance as opposed to dangerous attention tunneling or fixation. A task flow diagram represents the operator tasks. Interactions between the pilot and the instrumentation are used to estimate the probability distribution of the task the pilot is currently conducting, and physiological measures including electroencephalogram (EEG) and functional near-infrared spectroscopy (fNIRs) are used to determine neuroactivity to reduce the probability of false positives and increase the accuracy of the pilot vigilance monitoring system.

Referring to FIG. 1, a block diagram of a system 100 suitable for implementing embodiments of the incentive concepts disclosed herein is shown. The system 100 includes a processor 102, memory 104 in data communication with the processor 102 for storing processor executable code, one or more eye tracking sensors/cameras 108 for receiving eye tracking data stream, and one or more physiological sensors 110. Physiological sensors 110 may include devices such as an electroencephalograph (EEG), functional near-infrared spectroscopy (fNIRs), or any other such biometric data sensing device.

In at least one embodiment, the eye tracking sensors 108 record eye movement/gaze of a pilot and eye lid position. The processor executable code configures the processor 102 to continuously log the eye tracking data in a data storage element 106. The processor 102 analyzes the eye tracking data to identify gaze and pupil dynamics (e.g., pupil response and changes over time).

Eye tracking data are correlated with discreet portions of a training scenario or task, and/or specific stimuli such as instrument readings, alerts, or the like. The processor 102 determines whether the eye tracking data indicates attention to certain instrumentation within bounds of acceptable attention. In some instances, specific limitations to the amount of time a user spends observing an instrument may trigger "fixation" or "attention tunneling" warnings from an attention monitoring system. For tasks with heightened informational requirements, such limitations may be insufficient. The processor 102 compares the user's gaze duration/attention to a particular instrument or set of instruments to task specific thresholds or probabilities to determine if the duration is likely the result of the ordinary execution of the task, or if fixation is likely. Task specific thresholds may be defined with respect to similar, previously executed tasks, either by the same user or experts in the field.

The processor 102 may also receive physiological data from one or more physiological sensors 110. In at least one embodiment, the processor 102 correlates eye tracking data (including at least gaze and pupil dynamics) with physiological data. The processor 102 may compare the eye tracking and physiological data to stored profiles. Such profiles may be specific to the user and indicate a user specific maximum threshold. Alternatively, or in addition, the profiles may represent some standard maximum time. Alternatively, thresholds may be defined by probability of fixation rather than a maximum threshold time.

In at least one embodiment, the processor 102 may alert a remote party such as ground control personnel via a wireless communication device 112. Alternatively, or in addition, the processor 102 may render the determination of fixation on a display 114. For example, in a training scenario, an instructor may continuously monitor attention time on the display 114.

In at least one embodiment, the processor 102 transfers the stored eye tracking data and other correlated system and task data to an offline storage device for later analysis and correlation to historic data and other outside factors such as crew rest, crew sleet rhythms, flight schedules, etc. Such transfer may be in real time via the wireless communication device 112.

Figure 2:
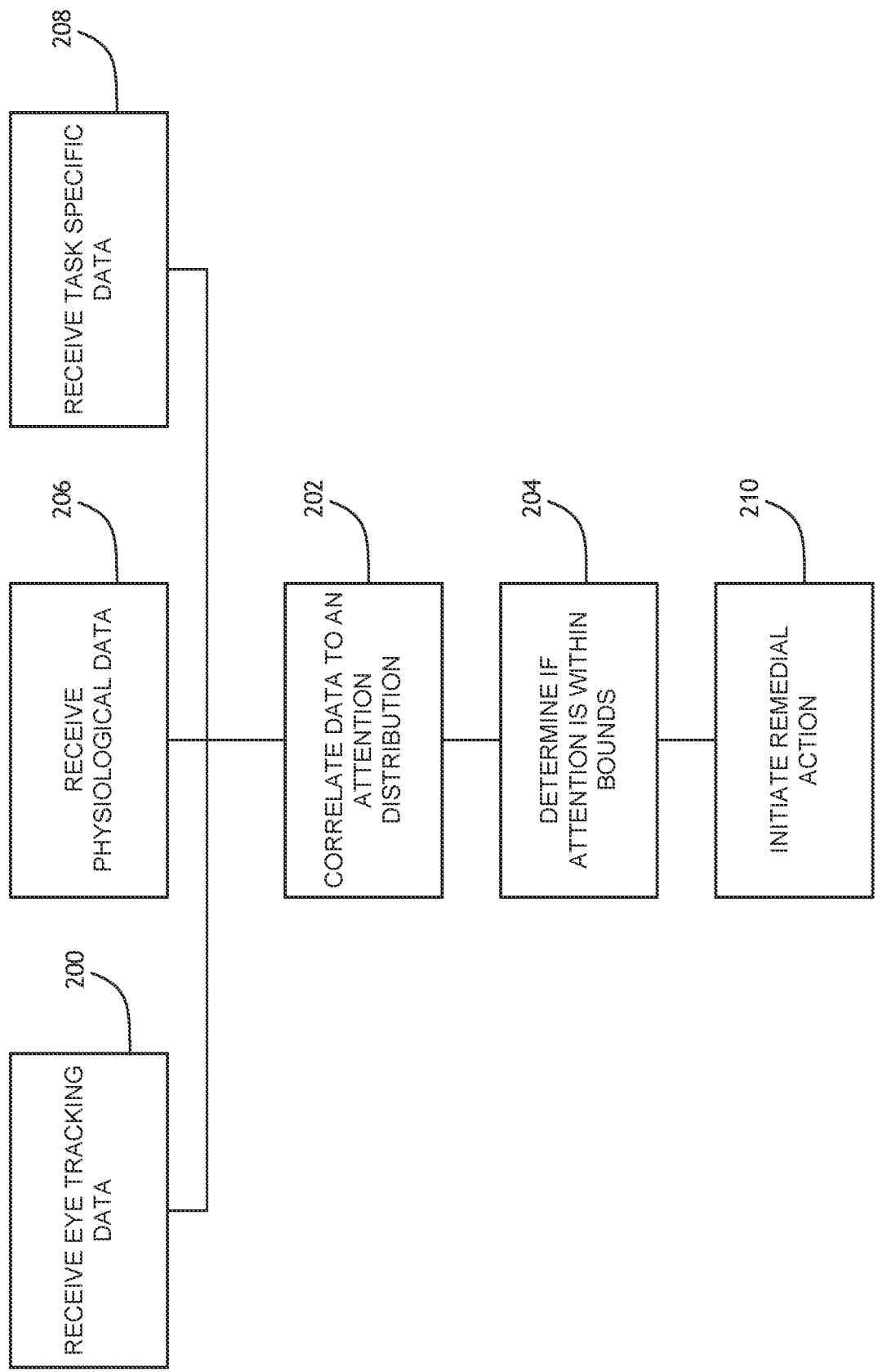
FIG. 2 shows a flowchart of an exemplary embodiment of the inventive concepts disclosed herein.

Referring to FIG. 2, a flowchart of an exemplary embodiment of the inventive concepts disclosed herein is shown. A computer system implementing embodiments of the inventive concepts disclosed herein receives 200 an image stream corresponding to eye tracking data from one or more vision-based sensors. The eye tracking data are continuously logged and correlated 202 to an attention distribution specific to a flight task or an individual duty schedule of the user/pilot.

In at least one embodiment, the eye tracking data is analyzed to determine 204 if the user's attention to a particular instrument is appropriate or excessive for the task. Such analysis may include processing via machine learning, neural network algorithms. Tasks may define specific attention boundaries either in terms of absolute time spent viewing an instrument, or as a probability of attention tunneling based on time. In at least one embodiment, such determination 204 may include factors specific to the task 208; for example, when observing a radar, the number of targets presented may impact the amount of time reasonably necessary to absorb the information presented.

In at least one embodiment, the system receives 206 physiological data from one or more physiological sensors such as an EEG and/or an fNIRs. Such physiological data provides the addition metric of neuroactivity when determining if the gaze time is appropriate for the task.

In at least one embodiment, if the system determines 204 that fixation or attention tunneling is occurring, the system may initiate 210 some remedial action. For example, the system may render warning messages to the user or contact a third party. Alternatively, or in addition, where an automation system exists, the monitoring system may automatically increase levels of automation to reduce user work load.

Figure 3A:
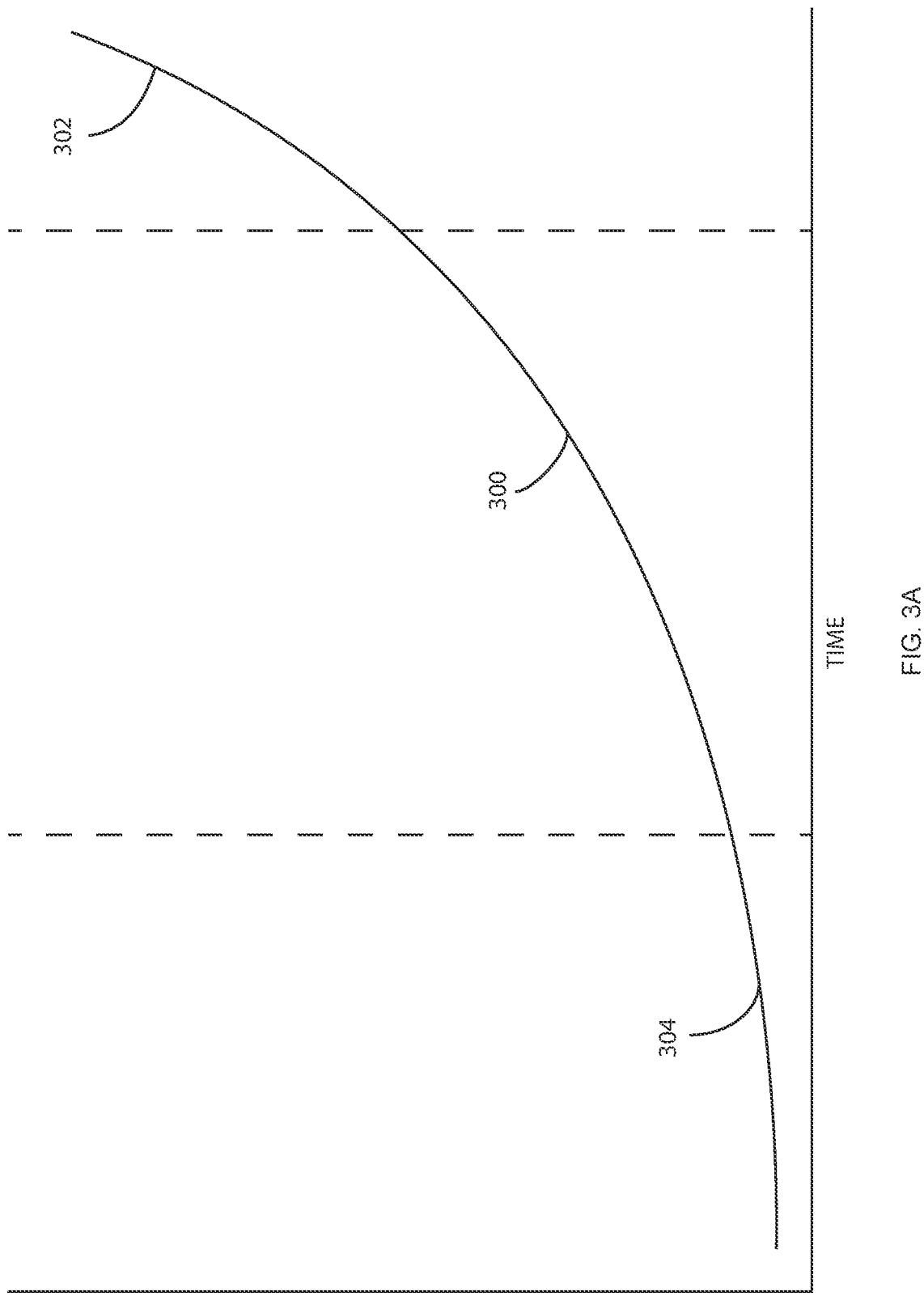
FIG. 3A shows a graph of gaze time bounded by acceptable attention levels according to an exemplary embodiment.
Figure 3B:
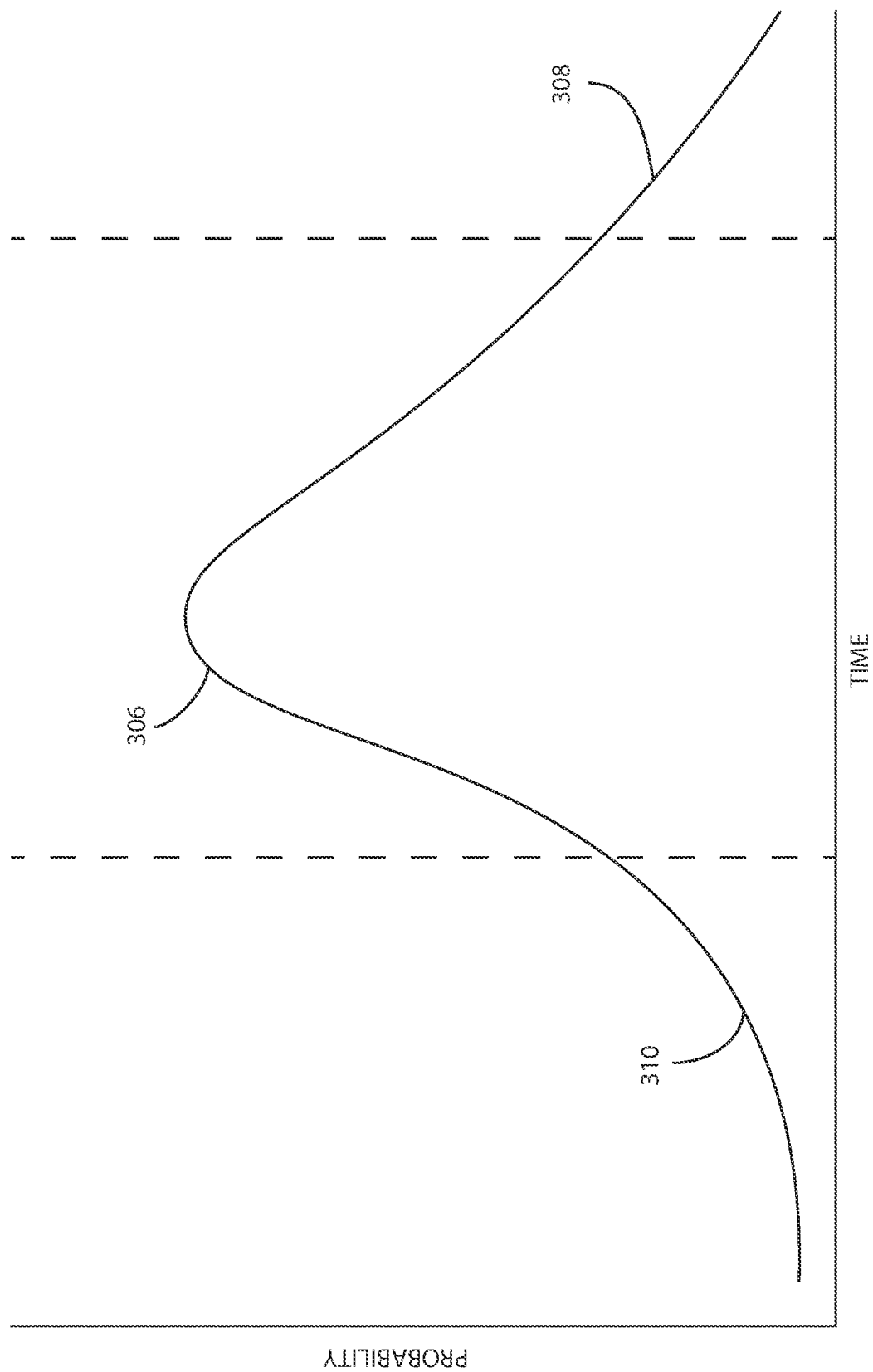
FIG. 3B shows a graph of gaze time probability for acceptable attention levels according to an exemplary embodiment.

Referring to FIGS. 3A and 3B, graphs of gaze time bounded by acceptable attention levels and gaze time probability for acceptable attention levels according to exemplary embodiments are shown. For any specific task or distinct portion of a task, an attention monitoring system tracking the gaze of a user determine the length of time the user has focused on a specific instrument. Each task or distinct portion may define a duration of acceptable attention 300 and a duration of excessive attention 302. Such durations may generally correspond to levels exhibited by experts performing similar tasks, or they may be specific to the user. For example, the gaze of a user may be recorded over time for similar tasks to produce a user specific profile; the threshold between the duration of acceptable attention 300 and the duration of excessive attention 302 may be specific to that user.

In at least one embodiment, the attention monitoring system may also define a duration of inadequate attention 304 corresponding to some minimum threshold necessary to acquire vital information from the instrument. Such minimum threshold may be defined by previous examples of experts performing similar tasks or by the user specific profile.

In at least one embodiment, the monitoring system may define user attention with respect to probability distribution. The system may define a probability curve of appropriate attention with respect to time. Boundary thresholds divide acceptable probabilities 300 from unacceptable probabilities 308, 310. The probability curve may be determined with respect to prior recorded instances of the same or similar tasks.

Figure 4:
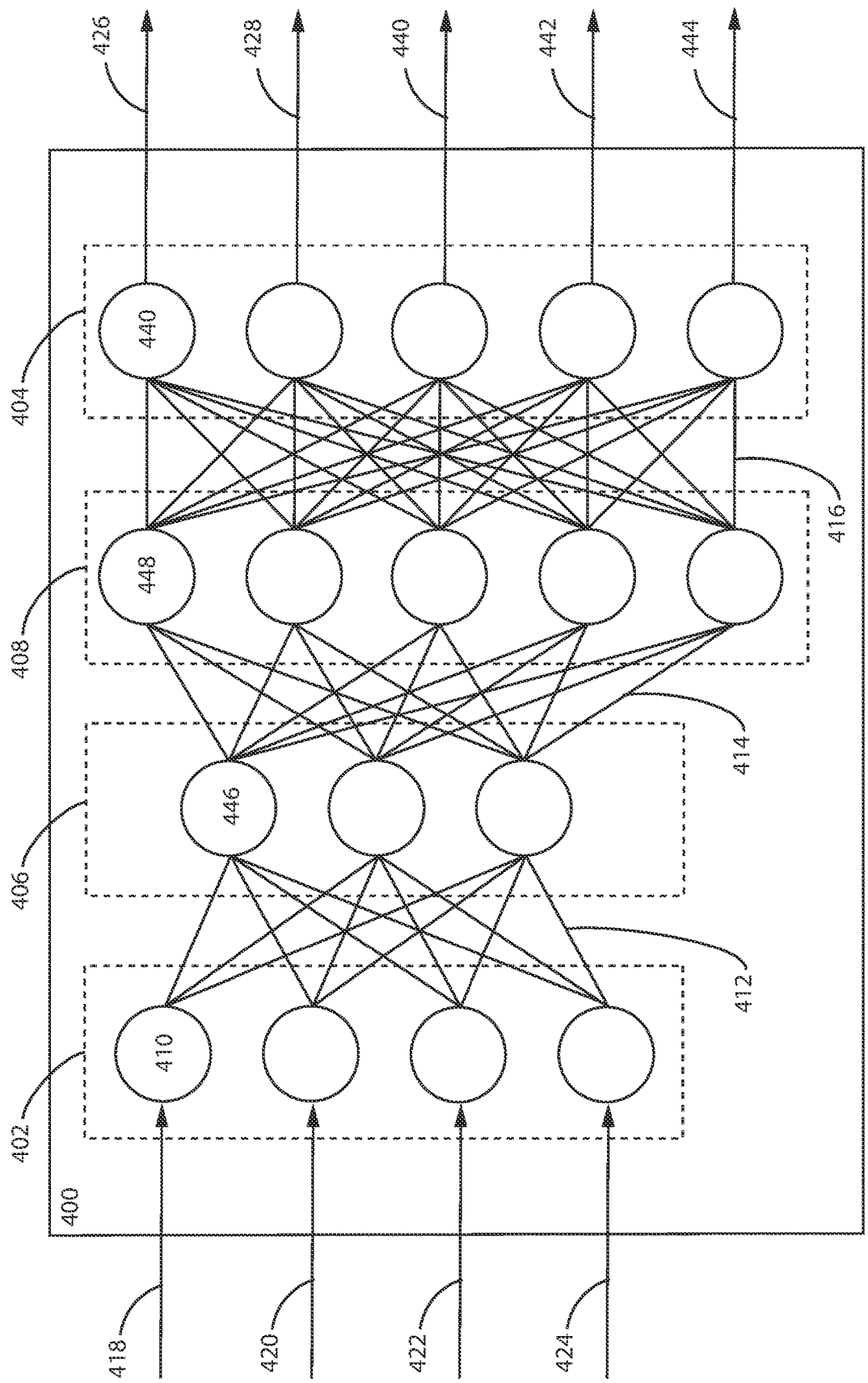
FIG. 4 shows a block diagram of a neural network according an exemplary embodiment of the inventive concepts disclosed herein.

Referring to FIG. 4, a block diagram of a neural network 400 according an exemplary embodiment of the inventive concepts disclosed herein is shown. The neural network 400 comprises an input layer 402 that receives external inputs (including physiological signals, such as EEG and fNIRs, eye tracking data, and potentially user or task specific profiles), and output layer 404, and a plurality of internal layers 406, 408. Each layer comprises a plurality of neurons or nodes 410, 436, 438, 440. In the input layer 402, each node 410 receives one or more inputs 418, 420, 422, 424 corresponding to a digital signal and produces an output 412 based on an activation function unique to each node 410 in the input layer 402. An activation function may be a Hyperbolic tangent function, a linear output function, and/or a logistic function, or some combination thereof, and different nodes 410, 436, 438, 440 may utilize different types of activation functions. In at least one embodiment, such activation function comprises the sum of each input multiplied by a synaptic weight. The output 412 may comprise a real value with a defined range or a Boolean value if the activation function surpasses a defined threshold. Such ranges and thresholds may be defined during a training process. Furthermore, the synaptic weights are determined during the training process.

Outputs 412 from each of the nodes 410 in the input layer 402 are passed to each node 436 in a first intermediate layer 406. The process continues through any number of intermediate layers 406, 408 with each intermediate layer node 436, 438 having a unique set of synaptic weights corresponding to each input 412, 414 from the previous intermediate layer 406, 408. It is envisioned that certain intermediate layer nodes 436, 438 may produce a real value with a range while other intermediated layer nodes 436, 438 may produce a Boolean value. Furthermore, it is envisioned that certain intermediate layer nodes 436, 438 may utilize a weighted input summation methodology while others utilize a weighted input product methodology. It is further envisioned that synaptic weight may correspond to bit shifting of the corresponding inputs 412, 414, 416.

An output layer 404 including one or more output nodes 440 receives the outputs 416 from each of the nodes 438 in the previous intermediate layer 408. Each output node 440 produces a final output 426, 428, 430, 432, 434 via processing the previous layer inputs 416, the final output 426, 428, 430, 432, 434 corresponding to a characterization of a set of physiological data as within some threshold probability of appropriate attention. Such outputs may comprise separate components of an interleaved input signal, bits for delivery to a register, or other digital output based on an input signal and DSP algorithm. In at least one embodiment, each node 410, 436, 438, 440 in any layer 402, 406, 408, 404 may include a node weight to boost the output value of that node 410, 436, 438, 440 independent of the weighting applied to the output of that node 410, 436, 438, 440 in subsequent layers 404, 406, 408. It may be appreciated that certain synaptic weights may be zero to effectively isolate a node 410, 436, 438, 440 from an input 412, 414, 416, from one or more nodes 410, 436, 438 in a previous layer, or an initial input 418, 420, 422, 424.

In at least one embodiment, the number of processing layers 402, 404, 406, 408 may be constrained at a design phase based on a desired data throughput rate. Furthermore, multiple processors and multiple processing threads may facilitate simultaneous calculations of nodes 410, 436, 438, 440 within each processing layers 402, 404, 406, 408.

Layers 402, 404, 406, 408 may be organized in a feed forward architecture where nodes 410, 436, 438, 440 only receive inputs from the previous layer 402, 404, 406 and deliver outputs only to the immediately subsequent layer 404, 406, 408, or a recurrent architecture, or some combination thereof.

Embodiments of the inventive concepts disclosed herein are critical to enabling reduced crew or single pilot operations, and will provide independent measures necessary to facilitate reduced crew in the cockpit by providing a means to identify when crew members are unable to continue safe flight and notify relief crew or activate automation. Furthermore, a training application may utilize embodiments of the inventive concepts to compare the small involuntary eye movements of a pilot-in-training to previously characterized professional pilot data patterns. Improved methods of assessing an operator's ability to acquire and maintain situation awareness is important for training. As such, it can serve as enabling technologies for single pilot operations or reduced crew operations.

It is believed that the inventive concepts disclosed herein and many of their attendant advantages will be understood by the foregoing description of embodiments of the inventive concepts disclosed, and it will be apparent that various changes may be made in the form, construction, and arrangement of the components thereof without departing from the broad scope of the inventive concepts disclosed herein or without sacrificing all of their material advantages; and individual features from various embodiments may be combined to arrive at other embodiments. The form herein before described being merely an explanatory embodiment thereof, it is the intention of the following claims to encompass and include such changes. Furthermore, any of the features disclosed in relation to any of the individual embodiments may be incorporated into any other embodiment.

What is claimed is:

1. A computer apparatus comprising:
   at least one eye tracking camera;
   one or more physiological data recording devices including at least a functional near-infrared spectroscope (fNIRs) and an electroencephalogram (EEG); and
   at least one processor in data communication with a memory storing processor executable code; and
   wherein the processor executable code configures the at least one processor to:
      receive an image stream from the at least one eye tracking camera;

receive physiological data from the one or more physiological data recording devices; and identify gaze and pupil dynamics from the image stream;

correlate the physiological data with the gaze and pupil dynamics;

monitor neuroactivity via the fNIRs and EEG to reduce a probability of a false positive for fixation;

correlate the gaze and pupil dynamics with a current task; and determine when a duration of gaze is within a threshold of acceptable attention for the current task with reference to the physiological data.

2. The computer apparatus of claim 1, wherein:

the processor executable code further configures the at least one processor to receive a task or user specific profile of gaze, pupil dynamics, and physiological data; and determining when the duration is within a threshold of acceptable attention includes reference to the task or user specific profile.

3. The computer apparatus of claim 1, further comprising a data storage element in data communication with the at least one processor, wherein the processor executable code further configures the at least one processor to continuously store the gaze and pupil dynamics in the data storage element.

4. The computer apparatus of claim 3, wherein the processor executable code further configures the at least one processor to:

analyze the stored gaze and pupil dynamics over time to identify a user specific profile of a user; and subsequently compare the gaze and pupil dynamics to the user specific profile.

5. The computer apparatus of claim 1, wherein the processor executable code further configures the at least one processor as a machine learning neural network.

6. A method comprising:

receiving an image stream from at least one eye tracking camera;

receiving physiological data from one or more physiological data recording devices including at least a functional near-infrared spectroscope (fNIRs) and an electroencephalogram (EEG); and identifying gaze and pupil dynamics from the image stream;

correlating the physiological data with the gaze and pupil dynamics;

monitoring neuroactivity via the fNIRs and EEG to reduce a probability of a false positive for fixation;

correlating the gaze and pupil dynamics with a current task; and determining when a duration of gaze is within a threshold of acceptable attention for the current task with reference to the physiological data.

7. The method of claim 6, further comprising receiving a task or user specific profile of gaze, pupil dynamics, and physiological data, wherein determining when the duration of gaze is within the threshold includes reference to the task or user specific profile.

8. The method of claim 6, further comprising continuously storing the gaze and pupil dynamics in a data storage element.

9. The method of claim 8, further comprising:

analyzing the stored gaze and pupil dynamics over time to identify a user specific profile of a user; and subsequently comparing the gaze and pupil dynamics to the user specific profile.

10. The method of claim 6, wherein determining when the duration of gaze is within the threshold includes comparing the duration to a probability distribution of previously recorded user's executing the current task.

11. The method of claim 6, further comprising initiating a remedial action when the gaze and pupil dynamics are characterized as stimuli triggered and no anticipatory response is identified.

12. A simulator comprising:

at least one eye tracking camera;

one or more physiological data recording devices including at least a functional near-infrared spectroscope (fNIRs) and an electroencephalogram (EEG); and at least one processor in data communication with a memory storing processor executable code; and wherein the processor executable code configures the at least one processor to:

receive an image stream from the at least one eye tracking camera;

receive physiological data from the one or more physiological data recording devices; and identify gaze and pupil dynamics from the image stream;

correlate the physiological data with the gaze and pupil dynamics;

monitor neuroactivity via the fNIRs and EEG to reduce a probability of a false positive for fixation;

correlate the gaze and pupil dynamics with a current task; and determine when a duration of gaze is within a threshold of acceptable attention for the current task with reference to the physiological data.

13. The simulator of claim 12, wherein:

the processor executable code further configures the at least one processor to receive a task or user specific profile of gaze, pupil dynamics, and physiological data; and determining when the duration is within a threshold of acceptable attention includes reference to the task or user specific profile.

14. The simulator of claim 12, further comprising a data storage element in data communication with the at least one processor, wherein the processor executable code further configures the at least one processor to continuously store the gaze and pupil dynamics in the data storage element.

15. The simulator of claim 12, wherein the processor executable code further configures the at least one processor to: analyze the stored gaze and pupil dynamics over time to identify a user specific profile of a user; and subsequently compare the gaze and pupil dynamics to the user specific profile.

* * * * *